United States Patent
Cheng et al.

(10) Patent No.: US 11,130,971 B2
(45) Date of Patent: Sep. 28, 2021

(54) BIOSLURRY-INDUCED WATER BARRIER AND PROCESS OF FORMING THEREOF

(71) Applicant: Nanyang Technological University, Singapore (SG)

(72) Inventors: Liang Cheng, Singapore (SG); Yang Yang, Singapore (SG); Jian Chu, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 16/652,628

(22) PCT Filed: Oct. 31, 2018

(86) PCT No.: PCT/SG2018/050551
§ 371 (c)(1),
(2) Date: Mar. 31, 2020

(87) PCT Pub. No.: WO2019/088925
PCT Pub. Date: May 9, 2019

(65) Prior Publication Data
US 2020/0318141 A1  Oct. 8, 2020

(30) Foreign Application Priority Data
Oct. 31, 2017  (SG) .............. 10201708948P

(51) Int. Cl.
*C12P 3/00* (2006.01)
*E02B 3/16* (2006.01)
(52) U.S. Cl.
CPC ............. *C12P 3/00* (2013.01); *E02B 3/16* (2013.01); *C12Y 305/01005* (2013.01)
(58) Field of Classification Search
CPC ............ C04B 28/10; C04B 2103/0001; C04B 24/126; C12Y 305/01005; C12P 3/00;
(Continued)

(56) References Cited

U.S. PATENT DOCUMENTS 3,108,441 A  10/1963  Watson
3,986,365 A  10/1976  Hughes
(Continued)

FOREIGN PATENT DOCUMENTS

CN  101302484 A  11/2008
GB  2202185 A  9/1988
(Continued)

OTHER PUBLICATIONS

Cheng et al.; Urease active bioslurry: a novel soil improvement approach based on microbially induced carbonate precipitation; Can. Geotech. J. vol. 53, 2016; pp. 1376-1385.
(Continued)

*Primary Examiner* — Carib A Oquendo
(74) *Attorney, Agent, or Firm* — Patterson + Sheridan, LLP

(57) ABSTRACT

Disclosed herein is a process of forming an inorganic water barrier layer on top of a porous substrate by means of microbially induced calcium carbonate or calcite precipitation (MICP), the process comprising the steps of: providing a porous substrate having a surface; depositing a urease-active slurry onto the surface of the porous substrate to form a bioslurry layer; and subjecting the bioslurry layer to one or more treatments with an aqueous solution comprising urea and a water barrier source material to convert the bioslurry layer into an inorganic water barrier layer. The process further comprises a step of covering the bioslurry layer with a layer of a porous material that has a surface, where the one or more treatments with an aqueous solution comprising urea and a water barrier source material are initially applied to the surface of the porous material. The porous material acts as a reservoir for the aqueous solution to sustain the biocementation of bioslurry into the desired inorganic water barrier layer.

21 Claims, 7 Drawing Sheets

(58) Field of Classification Search
CPC .. C12P 1/04; C09K 17/00; C09K 8/46; E02D 31/004; E02D 19/16; E02B 3/16
See application file for complete search history.

(56) References Cited

U.S. PATENT DOCUMENTS

| | | | |
|---|---|---|---|
| 4,202,413 | A | 5/1980 | Messenger |
| 4,344,722 | A | 8/1982 | Blais |
| 5,143,155 | A | 9/1992 | Ferris et al. |
| 5,396,749 | A | 3/1995 | Fukushima |
| 5,542,782 | A * | 8/1996 | Carter, Jr. .................. E02D 5/18 37/344 |
| 8,182,604 | B2 | 5/2012 | Kucharski et al. |
| 8,420,362 | B2 | 4/2013 | Crawford et al. |
| 10,450,695 | B2 * | 10/2019 | Dosier .................. A01K 61/54 |
| 2008/0245272 | A1 | 10/2008 | Kucharski et al. |
| 2018/0119185 | A1 * | 5/2018 | Kavazanjian ............. C12P 9/00 |
| 2019/0210924 | A1 * | 7/2019 | Royne .................... C04B 28/10 |

FOREIGN PATENT DOCUMENTS

| | | |
|---|---|---|
| WO | 1993000483 A1 | 1/1993 |
| WO | 1994019547 A1 | 9/1994 |

OTHER PUBLICATIONS

Chu et al.; Microbially InducedCalcium Carbonate Precipitation on Surface or in the Bulk of Soil, Geomicrobiology Journal, 29:6, pp. 544-549, DOI: 10.1080/01490451.2011.592929, 2012.
International Search Report and Written Opinion in related application PCT/SG2018/050551 dated Jan. 10, 2019.
De Muynck, et al.; Bacterial Carbonate Precipitation as an Alternative Surface Treatment for Concrete; Constr. Build. Mater., 2008, 22, 875-885.
De Muynck, et al.; Bacterial Carbonate Precipitation Improves the Durability of Cementitious Materials; Cem. Concr. Res., 2008, 38, 1005-1014.
Achal, et al.; Microbial Concrete: Way to Enhance the Durability of Building Structures; J. Mater. Civ. Eng., 2010, 23, 730-734.
Brooks, et al.; Inhibition of Bacterial U(VI) Reduction by Calcium; Environ. Sci. Technol., 2003, 37, 1850-1858.
Daniel, et al.; Compacted Clay Liners and Covers for Arid Sites; J. Geotech. Eng., 1993, 119, 223-237.
Daniel; Predicting Hydraulic Conductivity of Clay Liners; J. Geotech. Eng., 1984, 110, 285-300.
Miller et al.; A Catalyst for Regionalization of Rural Water Systems; J. Am. Water Resour. Assoc., 1988, 34, 677-686.
De Yoreo et al.; Shaping Crystals with Biomolecules; Science, 2004, 306, 1301-1302.
Teichert-Coddington, et al.; Hydrology of Fish Culture Ponds in Gualaca, Panama; Aquacultural Engineering, 1988, 7, 309-320.
Weisburd et al., Free Water Productivity Measurements in Leaky Mariculture Ponds; Aquacultural Engineering, 1990, 9, 377-403.
Stabnikov, et al.; Formation of Water-Impermeable Crust on Sand Surface Using Biocement; Cem. Concr. Res., 2011, 41, 1143-1149.
Thusyanthan, et al., Crack Initiation in Clay Observed in Beam Bending; Geotechnique, 2007, 57, 581-594.
Yang, et al.; Seepage Control in Sand Using Bioslurry; Constr. Build. Mater., 2019, 212, 342-349.
Whiffin, et al.; Microbial Carbonate Precipitation as a Soil Improvement Technique; Geomicrobiology J., 2007, 24, 417-423.
Van Paassen, et al.; Scale up of BioGrout: a biological ground reinforcement method; 17th International Conference on Soil Mechanics and Geotechnical Engineering, 2009, 2328-2333.
L. Cheng, et al.; Influence of Key Enviromental Conditions on Microbially Induced Cementation for Soil Stabilization; J. Geotech. Geoenviron. Eng., 2017, 143, 04016083.
Al-Thawadi et al.; Calcium Carbonate Crystals Formation by Ureolytic Bacteria Isolated from Australian Soil and Sludge; J. Adv. Sci. Eng. Res., 2012, 2, 12-26.

* cited by examiner

BIOSLURRY-INDUCED WATER BARRIER AND PROCESS OF FORMING THEREOF

FIELD OF INVENTION

This invention relates to a process of forming an inorganic water barrier layer on top of a porous substrate using urease-active bioslurry for water cutoff and seepage control in porous materials.

BACKGROUND

The listing or discussion of a prior-published document in this specification should not necessarily be taken as an acknowledgement that the document is part of the state of the art or is common general knowledge.

Seepage control is a common construction process for many infrastructures such as reservoirs, earth dams, tunnels and other underground constructions. It is well known that water will penetrate into the ground upon contact, resulting in the loss of water. This is particularly pronounced in sandy soil which has high water permeability. Various solutions, such as polymers, water-swellable colloidal clays, and multi-layer articles of manufacture, have been applied to the surface of soil to provide a waterproofing liner to prevent the penetration of water and toxic chemicals into the soil. Water-swellable clays, such as bentonite, can be directly applied to the soil surface or used with flexible, water-permeable fabric layers to reduce the permeability of the soil (see U.S. Pat. No. 3,986,365; GB 2,202,185 A; and U.S. Pat. No. 4,344,722). However, a problem associated with the use of such swellable clays is that they may shrink and produce cracks during dehydration, which may limit their applications.

Another drawback of the montmorillonite group of water-swellable clay is that the swelling capability in salt-contaminated water is substantially inhibited. Therefore, it is necessary to use a greater amount of clay to achieve the required degree of swelling. Alternatively, palygorskite clays can be used due to their better dispersal properties in salt water (see U.S. Pat. No. 4,202,413).

WO 1993000483A1 and WO 1994019547A1 disclose a system that uses a high pressure jet to shoot a slurry into the soil surrounding a hazardous waste site and liquefy the surrounding soil. The liquefied soil and slurry form a protective barrier after hardening. However, there are several drawbacks such as the disturbance to the ground or structures by the high pressure jets and the inability to control the uniformity of the treatment, which may also limit the application of the system.

Reduction of soil permeability can also be achieved by injecting chemicals and/or polymers into the pores of soil to reduce water seepage by reducing the water permeability of the soil. It has been discovered that water seepage through porous soils can be impeded by the formation of a sub-surface seal. For example, U.S. Pat. No. 3,108,441 discloses an approach to form such a subsurface seal by applying an aqueous wax dispersion to porous soils. The dispersion is able to penetrate the soils to form a wax seal below the soil surface.

In addition, polyurethane pre-polymer compositions have been widely used as grouts for sealing structures or for water flow cutoff to reduce water permeability of soils (for example, see U.S. Pat. No. 5,396,749).

In the recent years, biocementation and bioclogging of soil or rocks have attracted much attention as they are more environmentally-friendly as compared to the chemical methods. The process involves the use $CaCO_3$ crystals produced through microbially induced calcium carbonate precipitation (MICP) to consolidate loose sand or to reduce the porosity and permeability of soils (for examples, see V. S. Whiffin, et al., *Geomicrobiology J.*, 2007, 24, 417-423; L. A. van Paassen, et al., 17th *International Conference on Soil Mechanics and Geotechnical Engineering*, 2009, 2328-2333; W. De Muynck, et al., *Constr. Build. Mater.*, 2008, 22, 875-885; and W. De Muynck, et al., *Cem. Concr. Res.*, 2008, 38, 1005-1014).

MICP is a microbiological or enzymatic process that converts soluble calcium source into insoluble calcium carbonate crystals through the hydrolysis of urea (in the presence of ureolytic bacteria or urease) as depicted in the following reaction (V. Achal, et al., *J. Mater. Civ. Eng.*, 2010, 23, 730-734):

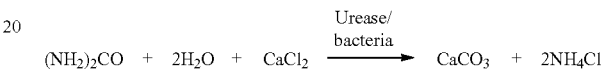

U.S. Pat. No. 8,182,604 discloses an approach of forming a high strength cement in a permeable particulate material, using a urease-producing microorganism, urea and calcium ions. U.S. Pat. No. 8,420,362 reveals a method to increase the concentration of microbially-induced calcium carbonate crystals in a geo-material that contains enriched indigenous microorganisms that are capable of hydrolysing urea to produce carbonate. All these aforementioned approaches focus on strength improvement rather than reducing the permeability of the soils.

U.S. Pat. No. 5,143,155 discloses an approach of using MICP in the presence of microorganisms to reduce the porosity or permeability of a sub-surface geological formation. However, this approach of using ureolytic bacteria or urease enzyme requires huge amount of cementation solution in order to achieve a significant reduction in permeability.

Further, Cheng and co-workers have devised a bioslurry approach for soil stabilisation, in which a urease-active slurry mainly consisting of $CaCO_3$ crystals with embedded urease-active bacteria was mixed with soil to reach uniform cementation (L. Cheng, et al., *J. Geotech. Geoenviron. Eng.*, 2017, 143, 04016083). However, the reduction of permeability was not significant, and complete water seepage control has not yet been achieved. Therefore, to form a dense $CaCO_3$ waterproofing barrier, a large amount of $CaCO_3$ crystals produced by the bacteria is required.

As such, there are several drawbacks associated with the conventional MICP process. Firstly, it is time consuming and costly due to the low efficiency of $CaCO_3$ precipitation (e.g. approximately 2% volume of solids is produced per volume of reagent solution used). Therefore, a large number of repeated treatments or the continuous circulation of the reagents is required, leading to an increase of cost and treatment time. Secondly, the resulting MICP-induced bio-cemented soil is often inhomogeneous, which may therefore limit the application of this process.

Given the above, there remains a need for an improved method to form an effective water barrier for water cutoff and seepage control in soil or rocks. The method has to be capable of producing a waterproofing layer that is durable, versatile and of extremely low water permeability. In addition, the method has to be efficient, cost-effective and should not require a large amount of reagents.

SUMMARY OF INVENTION

In a first aspect of the invention, there is provided a process of forming an inorganic water barrier layer on top of a porous material in need thereof, the process comprising the steps of:
(a) providing a porous substrate having a surface;
(b) depositing a urease-active slurry onto the surface of the porous substrate to form a bioslurry layer, the urease-active slurry comprising an aqueous suspension of particles of a water-insoluble inorganic material that is impregnated with urease-active bacteria, where the formed bioslurry layer substantially consists of the particles of the water-insoluble inorganic material; and
(c) subjecting the bioslurry layer to one or more treatments with an aqueous solution comprising urea and a water barrier source material to convert the bioslurry layer into an inorganic water barrier layer.

In embodiments of the first aspect of the invention:
(ai) the urease-active slurry may have a solid content of from 5 to 80% w/w, such as from 10 to 50% w/w, such as from 15 to 30% w/w, such as about 25% w/w;
(aii) the porous substrate may be one or more of the group consisting of a cracked inorganic water barrier layer, sand, soil and rocks;
(aiii) the water-insoluble inorganic material may be a metal carbonate (e.g. the metal of the metal carbonate is selected from one or more of the group consisting of Ca, Mg, and Al, such as $CaCO_3$);
(aiv) the water barrier source material may be selected from one or more of a metal chloride, acetate, lactate and nitrate (e.g. the metal in the water barrier source material is selected from one or more of the group consisting of Ca, Mg, and Al, such as Ca);
(av) the aqueous solution may comprise a molar ratio of urea:water barrier source material of from 1:20 to 20:1, such as from 1:5 to 5:1, such as 1:1;
(avi) the concentration of the urea and water barrier source material may independently be from 0.1 to 2 mol/L, such as from 0.5 to 2 mol/L, such as from 1.0 to 1.9 mol/L, such as from 1.5 to 1.8 mol/L, such as 1.6 mol/L, optionally wherein there may be an equimolar concentration of urea and water barrier source material in the aqueous solution;
(avii) the bioslurry layer and the inorganic water barrier layer may independently have a thickness of from 0.5 to 25 mm, such as from 1 to 20 mm, such as from 2 to 5 mm;
(aviii) the urease activity of the urease active slurry may be from 10 to 1500 U/g, such as from 25 to 750 U/g, such as from 50 to 300 U/g, such as from 55 to 150 U/g, such as around 60 U/g or around 240 U/g;
(aix) the urease-active bacteria may be a bacterial species that comprises a urease enzyme;
(ax) the bioslurry layer formed in step (b) of claim 1 may have a water permeability in the order of $10^{-5}$ m/s;
(axi) the modulus of rupture of the inorganic water barrier layer may be from 2 to 10 MPa, such as from 3 to 5 MPa, such as 4 MPa when measured using a sample of the layer that is 0.1 mm thick and has a length of from 6 to 10 cm and a width of from 3 to 5 cm.

In further embodiments combined with one or more of the embodiments (a) to (axi) above, the process may further comprise a step of covering the bioslurry layer of step (b) with a layer of a porous material that has a surface, where the one or more treatments of step (c) are initially applied to the surface of the porous material. In such embodiments:
(bi) the porous material may be one or more of the group consisting of sand, soil and rocks;
(bii) the water permeability of the resulting water barrier layer may be in the order of from $10^{-10}$ to $10^{-6}$ m/s, such as in the order of from $10^{-10}$ to $10^{-7}$ m/s, such as in the order of from $1\times10^{-9}$ to $1\times10^{-8}$ m/s;
(biii) the thickness of the porous material layer may be greater than 1.5 cm, such as from 2 to 20 cm, such as from 3 to 10 cm, such as from 3 to 6 cm;
(biv) when there are two or more treatments with an aqueous solution comprising urea and a water barrier source material in step (c) of claim 1, each treatment may be separated by a period of time of from 1 hour to 72 hours, such as from 6 hours to 48 hours, such as from 18 to 24 hours.

DESCRIPTION

Figure 1:
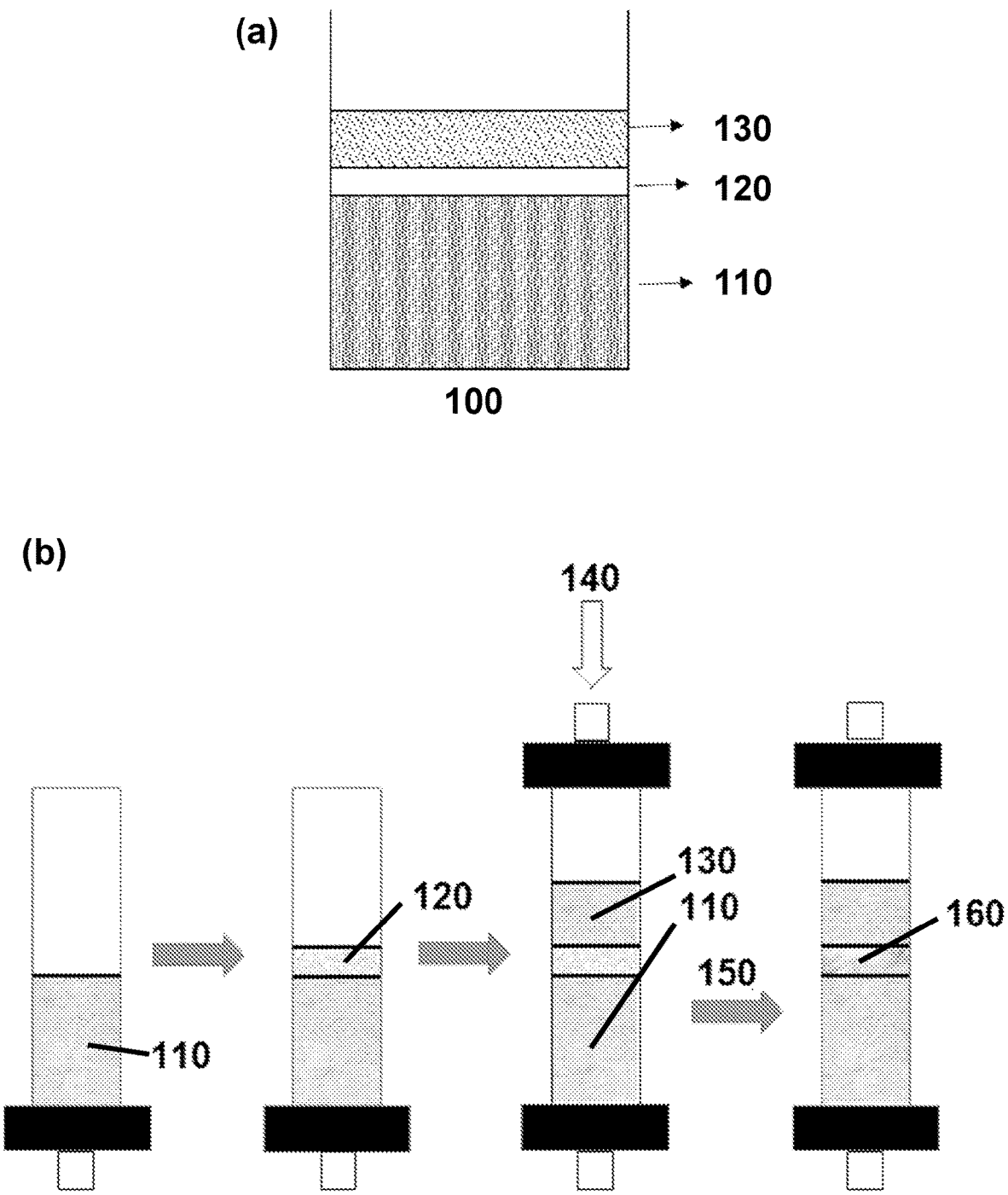
FIG. 1 Depicts the schematic representation of the layered setup 100 comprising a porous substrate 110, a bioslurry layer 120 and a top layer of porous materials 130 on top of 120; and (b) the process of forming 100 and to achieve the bioslurry-induced water barrier 160 via the addition of the cementation solution (mixture of urea and $CaCl_2$) solution) 140 over the top layer 130.

It has been surprisingly found that it is possible to form an inorganic barrier layer on a porous substrate in a simple and convenient process. This involves forming a bioslurry layer on the surface of the porous substrate, followed by treating the bioslurry layer with an aqueous solution of calcium ions and urea (also known as cementation solution). This allows the bioslurry to produce $CaCO_3$ crystals which act as binding materials to form a dense calcium carbonate water barrier of low water permeability. Thus, there is provided a process of forming an inorganic water barrier layer on top of a porous substrate in need thereof, the process comprising the steps of:

(a) providing a porous substrate having a surface;
(b) depositing a urease-active slurry onto the surface of the porous substrate to form a bioslurry layer, the urease-active slurry comprising an aqueous suspension of particles of a water-insoluble inorganic material that is impregnated with urease-active bacteria, where the formed bioslurry layer substantially consists of the particles of the water-insoluble inorganic material; and
(c) subjecting the bioslurry layer to one or more treatments with an aqueous solution comprising urea and a water barrier source material to convert the bioslurry layer into an inorganic water barrier layer.

When used herein, the "porous substrate" may be any suitable porous material that requires the introduction of a water barrier layer on a surface to prevent/reduce seepage or loss of water (e.g. on the bottom of a pond) or to prevent/reduce ingress of water into a cavity surrounded by the porous material (e.g. to prevent ingress of water into a cave or tunnel). For example, the porous substrate may be one or more of the group consisting of a cracked inorganic water barrier layer, sand, soil and rocks. When used herein, "sand", "soil" and "rocks" (i.e. "porous rocks") are intended to take their conventional meaning and cover all types of said materials suitably situated and suitable for application of the method described above. As will be appreciated, the "surface" of the porous substrate is any suitable surface that can be accessed and treated with the method described herein.

In situations where the porous substrate includes a previously-formed inorganic water barrier layer that has cracked, it may be possible to self-repair the layer if it still retains active bacteria, and this is discussed in more detail below. However, in a situation where the bacteria is dead, or insufficient bacteria remains alive, then the process may simply be repeated using the cracked inorganic water barrier layer itself as the substrate (or as part of the substrate) that is to be covered by a new inorganic water barrier layer. As will be appreciated, the previously-formed inorganic water barrier layer will be formed on a porous substrate itself, which may be selected from the group consisting of sand, soil and rocks or, in rare cases, yet a further cracked inorganic water barrier layer.

When used herein, "inorganic water barrier layer" refers to a layer of an inorganic material that is essentially insoluble in water at standard temperatures. Examples of such materials include insoluble metal carbonate materials, such as $CaCO_3$, $MgCO_3$, $Al_2CO_3$ and combinations thereof (e.g. $CaCO_3$). The inorganic water barrier layer may have any suitable thickness to provide the desired effect. For example from 0.5 to 25 mm, such as from 1 to 20 mm, such as from 2 to 5 mm.

The resulting inorganic water barrier layer may be relatively strong. For example, the modulus of rupture of the inorganic water barrier layer may be from 2 to 10 MPa, such as from 3 to 5 MPa, such as 4 MPa when measured using a sample of the layer that is 0.1 mm thick and has a length of from 6 to 10 cm and a width of from 3 to 5 cm. Details of the test to measure the modulus of rupture is provided in the examples section below.

When used herein "urease-active bacteria" refers to any suitable bacteria that contains a urease enzyme and which can hydrolyse urea. Many such bacteria exist and any that display the desired urease activity when combined with the bioslurry described herein may be used. A suitable, non-limiting example of such a bacteria is *Bacillus* sp. (DSM 23526).

When used herein "urease-active slurry" refers to a liquid (e.g. aqueous) suspension that comprises an amount of a water-insoluble inorganic material that is impregnated with urease-active bacteria. The "water-insoluble inorganic material" may be in a solid form, such as an amorphous form or a crystalline form. Examples of water-insoluble inorganic materials include insoluble metal carbonate materials, such as $CaCO_3$, $MgCO_3$, $Al_2CO_3$ and combinations thereof (e.g. $CaCO_3$). The water insoluble inorganic materials of the urease-active slurry are impregnated with urease-active bacteria, as defined above. As will be appreciated, the bacteria are still alive and are active, and so the bacteria either exist in pores within the solid water-insoluble inorganic materials or are held partially within said material in such a way that they can access nutrients and interact with the surrounding aqueous environment. Details of how the urease-active slurry are manufactured are provided in the examples section below. As will be appreciated, the urease-active slurry will contain a sufficient content of the solid water-insoluble inorganic materials to provide the desired effects. For example, the urease-active slurry may have a solid content (i.e. impregnated water insoluble inorganic materials) of from 5 to 80% w/w. Other suitable amounts of the water insoluble inorganic materials in the urease-active slurry include those from 10 to 50% w/w, such as from 15 to 30% w/w, such as about 25% w/w.

The urease-active slurry may have any suitable urease activity, provided that it is capable of utilising urea and a water barrier source material to form the inorganic water-insoluble barrier layer. For example, the urease activity of the urease active slurry may be from 10 to 1500 U/g, such as from 25 to 750 U/g, such as from 50 to 300 U/g, such as from 55 to 150 U/g, such as around 60 U/g or around 240 U/g. When used herein "x U/g" is used to mean that 1 g of dry bioslurry contains x U urease activity, where 1 U of urease activity is equivalent to 1 µmol of urea hydrolysed per minute.

When used herein "bioslurry layer" refers to the deposit of material left by the urease-active slurry after the liquid portion of the urease-active slurry has been allowed to drain into the porous substrate and/or evaporate off. As will be appreciated, the bioslurry layer is itself reasonably porous and it is the subsequent treatments of the bioslurry layer with an aqueous solution comprising urea and a water barrier source material that turn it into the desired inorganic water barrier layer. For example, the bioslurry layer may have a water permeability in the order of $10^{-5}$ m/s and may have a density of around 0.5 to 1.5 g/cm³ (e.g. around 1.3 g/cm³). In contrast, the resulting inorganic water barrier layer may have a water permeability in the order of $10^{-10}$ and a density of from about 2.2 to 2.3 g/cm$^3$. Thus, the urea and water barrier source material essentially fill in voids within the already-established bio-slurry layer and do not significantly change the size of said layer. As such, while the bioslurry layer may have any suitable thickness when established, this thickness is essentially identical to that of the resulting inorganic water barrier layer. As such, the bioslurry layer may have a thickness of from 0.5 to 25 mm, such as from 1 to 20 mm, such as from 2 to 5 mm when formed in step (b) of the process above.

When used herein "water barrier source material" is a water-soluble inorganic material that can be converted by the action of the urease-active bacteria into an insoluble inorganic material (i.e. the water-insoluble inorganic material(s) mentioned above). Any suitable soluble inorganic material may be used. Examples of suitable materials include, but are not limited to, metal chlorides, acetates, lactates, nitrates and combinations thereof. As will be appreciated, the metals may be selected from Ca, Mg, and Al (e.g. Ca).

The aqueous solution comprising urea and a water barrier source material will contain a suitable mixture of these materials. For example, the molar ratio of urea:water barrier source material may be from 1:20 to 20:1. Other suitable ranges may be from 1:5 to 5:1, and 1:1. For the avoidance of doubt, when numerical ranges are listed herein, the endpoints of related ranges (including single, related point values) may be combined to provide further ranges that are explicitly contemplated herein. For example, in the above ranges listed, the following ranges are explicitly intended to be disclosed herein: 1:20 to 20:1, 1:20 to 1:5, 1:20 to 5:1, 5:1 to 20:1, 1:20 to 1:1, 1:5 to 1:1, 1:1 to 5:1 and 1:1 to 20:1.

The aqueous solution comprising urea and a water barrier source material will also contain a suitable concentration of these materials. Each of urea and the water barrier source material may independently have a concentration of from 0.1 to 2 mol/L, such as from 0.5 to 2 mol/L. such as from 1.0 to 1.9 mol/L, such as from 1.5 to 1.8 mol/L, such as 1.6 mol/L. As will be appreciated "independently" means that urea and water barrier source material may have differing concentrations, but they may also have the same concentration (i.e. they have an equimolar concentration, resulting from a 1:1 molar ratio).

In the method described above, the application of the aqueous solution comprising urea and a water barrier source material may be conducted in any suitable manner. For example, the aqueous solution may be sprayed onto the bioslurry layer continually for an extended period of time to harden it. However, as shown in the examples below, while this does provide a functioning inorganic water barrier layer, the water permeability is relatively high (e.g. in the order of $10^{-5}$ m/s). It has been unexpectedly found that adding a layer of a porous material on top of the bioslurry layer enables one to obtain an inorganic water barrier layer with a water permeability in the order of at least $10^{-6}$ m/s. Without wishing to be bound by theory, it is believed that the introduction of a top layer of a porous material acts as a reservoir for the aqueous solution to sustain the biocementation of bioslurry into the desired inorganic water barrier layer. This not only reduces the water permeability of the resulting barrier layer, but also makes the process much more convenient, as there is no need to continually add the aqueous solution by spraying. Instead, a suitable amount of the aqueous solution (e.g. 1 void based on the porous material top layer) may be added and left to react with the bioslurry/intermediate water barrier layer.

Thus, in the context of the process of steps (a) to (c) above, the process may further comprise a step of covering the bioslurry layer of step (b) with a layer of a porous material that has a surface, where the one or more treatments of step (c) are initially applied to the surface of the porous material. Any suitable porous material may be used. Examples of such porous materials include, but are not limited to sand, soil and rocks, as defined above. Other materials that may be used as the porous material include a sponge or geotextile material (i.e. a permeable fabric). Any suitable thickness of the porous material top layer may be used. For example, this top layer may have a thickness of greater than 1.5 cm, such as from 2 to 20 cm, such as from 3 to 10 cm, such as from 3 to 6 cm. It is noted that a thickness of around 2 or 3 cm appears to be sufficient to maximise the reduction of water permeability of the resulting inorganic water barrier layer, though using a top layer thicker than about 2 or 3 cm does not appear to substantially affect the resulting water permeability. The use of the layer of porous material on top of the bioslurry layer may provide a water permeability for the resulting water barrier layer in the order of from $10^{-10}$ to $10^{-6}$ m/s, such as in the order of from $10^{-10}$ to $10^{-7}$ m/s, such as in the order of from $1\times10^{-9}$ to $1\times10^{-8}$ m/s. This is significantly better than simply applying the aqueous solution of urea and water barrier source material onto the bioslurry layer directly.

As will be appreciated, the application method of the aqueous solution comprising urea and a water barrier source material is not particularly limited when there is a layer of porous material on top of the bioslurry layer. For example, the solution may simply be poured onto the layer, or may be deposited by methods such as tricking or flushing. It is not believed that the manner of the addition of the aqueous solution to the top layer of porous material significantly impacts the resulting inorganic water barrier layer's properties.

As noted above, one of the advantages of the use of a layer of porous material on top of the bioslurry layer is that it enables one to add a quantity of aqueous solution to the top layer, which then interacts with the bioslurry layer to fill in voids in said layer with an insoluble inorganic material over a period of time. As will be appreciated, while a single addition of the aqueous solution will fill in voids within the bioslurry layer and therefore make it into a water barrier layer, the resulting layer may still have sub-optimal water permeability and strength for the desired role it is to perform. In this case, it is possible to treat the intermediate material again with the aqueous solution for as many times as required until the desired properties are obtained. Such re-additions of material will typically be separated by a suitable period of time to ensure that the urea and water barrier source material have been used up and that the water has substantially been removed (e.g. by drainage or by evaporation). For example, when there are two or more treatments with an aqueous solution comprising urea and a water barrier source material source in step (c) of the method, each treatment is separated by a period of time of from 1 hour to 72 hours, such as from 6 hours to 48 hours, such as from 18 to 24 hours. In addition, and as shown herein, the use of a layer of porous material on top of the bioslurry layer results in a water barrier having improved impermeability and strength compared to a barrier formed in the absence of such a top layer of porous material.

As mentioned above, it is possible to replace a cracked inorganic water barrier layer with a new layer by simply using the cracked water barrier layer as the porous substrate (or part thereof). However, this need only occurs if the bacteria that was imbedded in the original solid, insoluble inorganic materials of bioslurry layer are dead. In situations where the bacteria are still active, it is possible to simply make use of step (c) to add the aqueous solution comprising urea and a water barrier source material to cracked water barrier layer to heal it. As will be appreciated, it is difficult to predict when bacteria imbedded within the inorganic barrier layer will become fully inactive. This is especially true for urease-active bacteria that can form spores and "sleep" for years before being "awakened" by the introduction of suitable nutrients. As such, the simplest way to determine whether the bacteria are still active or not is to add the aqueous solution comprising urea and a water barrier source material to the cracked layer and see if the water permeability decreases. If so, the bacteria are still active and the step (c) may be repeated as described above until the desired water permeability/strength is re-established. In the event that the cracked water barrier layer's water permeability does not improve, then the process outlined above can be conducted in full. Of course, in a situation where the water barrier layer has been cracked just after formation due to mechanical impact or the like, the bacteria will certainly still be active and only step (c) of the above process is needed to heal the cracked layer. Advantageously, the ability to replace a cracked inorganic water barrier layer can increase the lifespan of the pre-existing water barrier, or to allow a non-functional cracked water barrier to be reused. This can result in a cost-saving, as less new material needs to be supplied.

Further aspects and embodiments of the invention are described below in the following non-limiting examples.

EXAMPLES

The current invention relates to a process of forming a bioslurry-induced $CaCO_3$ water barrier on top of a porous substrate, which first requires a layered setup 100 as shown in FIG. 1a. FIG. 1a depicts the schematic illustration of the cross-section of the setup 100 with the porous substrate 110 forming the base, followed by a layer of the bioslurry 120, and lastly a top layer of porous materials 130 on top of 120.

As shown in FIG. 1b, the mixture of urea and $CaCl_2$) solution 140 (also known as cementation solution) is then added over the top layer 130, which allows the solution to pass through 130 before reaching the bioslurry layer 120. The interaction of the bioslurry with the cementation solution produces $CaCO_3$ crystals via the microbially induced calcium carbonate precipitation (MICP) process 150. Thereafter, the bioslurry layer 120 is hardened to form a bioslurry-induced water barrier 160 which consists of a dense $CaCO_3$ crystal layer with low permeability.

Figure 2:
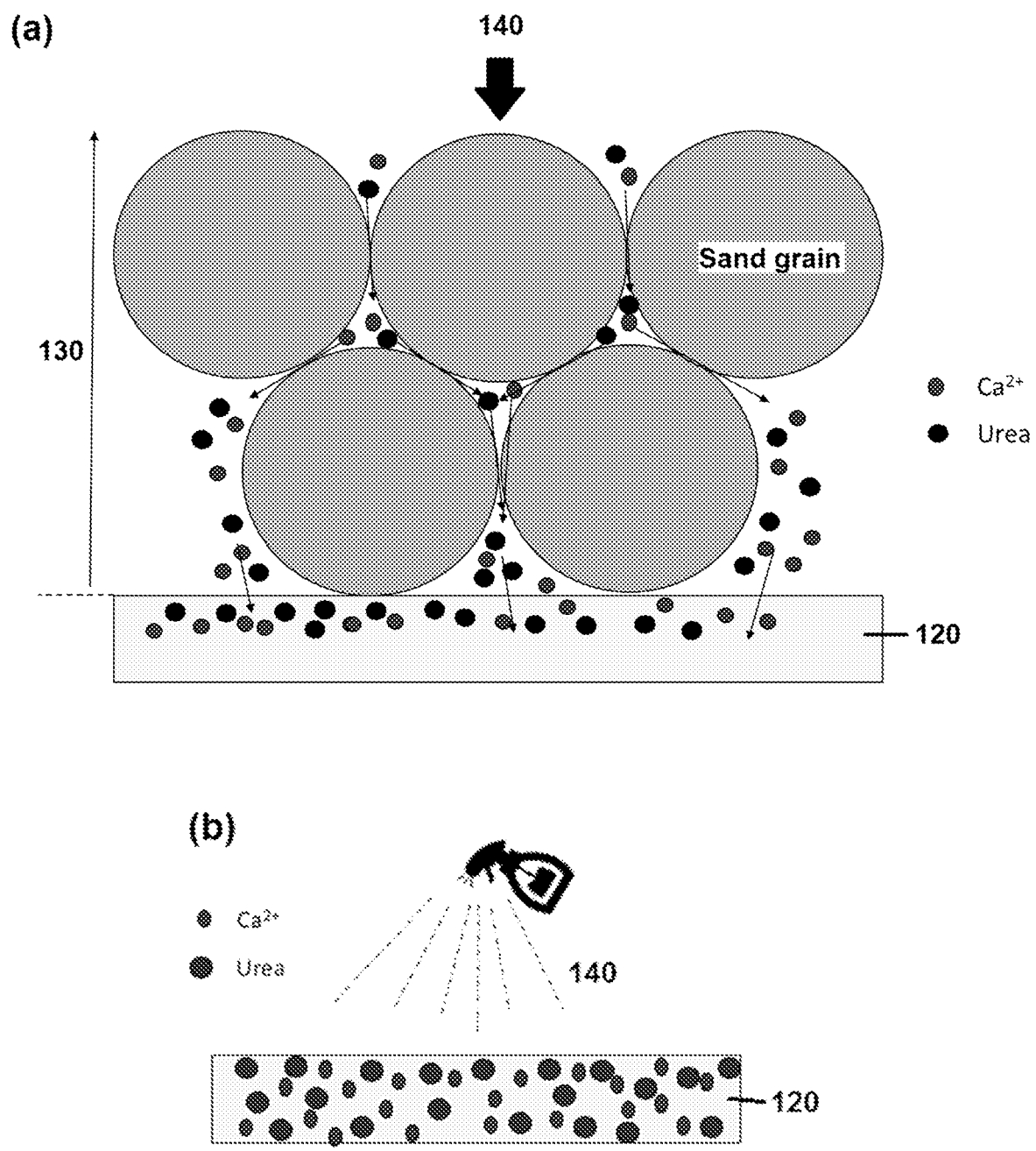
FIG. 2 Depicts the two methods of adding the cementation solution (mixture of urea and $CaCl_2$) solution) 140 to the bioslurry layer 120: (a) the addition of the cementation solution 140 onto the top layer of porous materials 130, which allows the diffusion of calcium ions and urea through the pores of 130 to reach the bioslurry layer 120; and (b) the direct addition of a cementation solution 140 onto the bioslurry layer 120, without the top layer of porous materials 130.

As depicted in FIG. 2a, the formation of the bioslurry-induced water barrier is achieved by periodically introducing the cementation solution 140 to the top layer of porous materials 130 until it is full saturated. The capillary force of the porous materials allows significant retention of the mixed solution of urea and calcium source inside the top layer 130. Therefore, the urease-active bio-slurry layer can receive continuous supply of urea and $Ca^{2+}$ ions through the diffusion of chemicals as shown in FIG. 2a.

Alternatively, the formation of the $CaCO_3$ water barrier can also be achieved without the top porous materials layer 130. This involves slowly trickling or spraying the cementation solution 140 directly onto the bioslurry layer 120 (FIG. 2b).

Materials

Ottawa sand, specified by ASTM C 788, was used in the experiments. The Ottawa sand has the following grain size distribution: >1.18 mm, 0%; 0.6-1.18 mm, 3.22%; 0.425-0.6 mm, 26.05%; 0.3-0.425 mm, 43.03%; 0.15-0.3 mm, 27.08%; and <0.15 mm, 0.62%.

Method

Permeability Measurement

Laboratory determination of the permeability of the sand columns were conducted using the falling-head permeability test in accordance with ASTM D5084. All permeability measurements were carried out twice and the average values were reported, unless otherwise stated.

Urease Activity Measurement

The urease activity of the bioslurry is defined as the hydrolysis rate of urea per gram of the dry bioslurry. This was accomplished by measuring the amount of ammonium produced per minute of a mixture which contains 2 mL of bioslurry (about 25% solid content), 18 mL of deionised water and 20 mL of urea (3 M). A conductivity meter was used to determine the change in the ammonium concentration, with the mixture stirring at a speed of 400 rpm. The specific urease activity of bioslurry is denoted as urease activity per gram (U/g), where 1 U of urease activity is equivalent to 1 μmol of urea hydrolysed per minute. After determining the urease activity of the bioslurry, the crystals were rinsed with deionised water, followed by drying in the oven at 105° C. for 24 h. The weight of the residual dried solid was recorded and used for calculating the corresponding specific urease activity.

Cultivating the Ureolytic Bacteria

The ureolytic bacteria used was isolated from activated sludge obtained from a local wastewater treatment plant. The urease-active bacteria was identified as *Bacillus* sp. strain (DSM 23526), which was cultivated in a sterile aerobic batch growth medium consisting of 20 g/L of yeast extract, 10 g/L of ammonium chloride and 0.1 mmol/L of $NiCl_2$ at pH 9.

The cultivated bacterial culture was collected at the stationary phase of culture growth after 24 h of cultivation at 28° C. Alternatively, cultivation of the bacteria was conducted at 28° C. in a 1 L flask on an orbital shaker at an agitation rate of 600 rpm. The bacteria culture was collected after 48 h of cultivation and store at 4° C. prior to use. The optical density ($OD_{600}$) of the collected bacterial culture varied between 2 and 5, and the urease activity was determined using a conductivity meter to be approximately 5-30 U/mL (1 U=1 μmol of urea hydrolysed in a minute). The urease activity was adjusted to approximately 10 mM urea/min (i.e. 10 U/mL) using deionsed water prior to use.

General Method for Preparing the Urease-Active Bio-Slurry

The urease-active bio-slurry was then prepared by adding specific amounts of urea and calcium chloride (in equal moles) into the collected bacterial culture (100 mL) to reach target concentrations of the urea or calcium chloride in the range from 0.05 to 1.5 mol/L. The mixture was then stirred at a speed of 600 rpm for about 24 h.

In the presence of the urea and $Ca^{2+}$, $CaCO_3$ crystals were formed due to hydrolysis of urea by the ureolytic bacteria and these crystals were precipitated out of the aqueous phase together with the bacterial cells. When the added urea and $CaCl_2$) were completely consumed (determined by measuring the amount of ammonium produced in the solution), the mixture was allowed to settle for 6 h. After settlement, the clear layer of supernatant was discarded and the settled crystals (urease-active bio-slurry) were then harvested. The produced urease-active bio-slurry possessed solid contents of about 5 to 80% w/w and urease activities of about 10-1500 U/g.

Example 1. Preparation of the Urease-Active Bioslurry

The urease-active bioslurry was prepared by supplying 44.4 g of solid calcium chloride and 24 g of solid urea into 1 L of the harvested bacteria culture, such that the concentrations of the calcium chloride and urea were 0.4 M. This was followed by 24 h of stirring at a speed of 600 rpm. When the added calcium chloride and urea have been completely consumed, a large amount of calcium carbonate crystals were precipitated with high urease activity bacteria cells imbedded within the crystals.

To maximise the output and urease activity of the bio-slurry, the suspension was allowed to settle for at least 4 h, with the clear supernatant (about 900 mL) removed and the residual (with the settled crystals) collected. The residual mixture (urease-active bioslurry) was stored in a refrigerator at 4° C. prior to use. The solid content of the residual mixture was determined to be 25±3% (w/w). The urease activity of the resulting bioslurry was about 44 U/g (0.44 ms/min/g).

Example 2. Effect of the Concentrations of Cementation Solution ($Ca^{2+}$ and Urea) on the Chemical Conversion of Calcium Ions to Calcium Carbonate by the Urease-Active Bioslurry To determine the optimised concentration of cementation solution for the maximum conversion of calcium ions to calcium carbonate, the following studies were conducted, via the steps below.
1) Five centrifuge tubes were first filled with 4 g (25% solid content, urease activity=44 U/g) of the bioslurry respectively, and centrifuged at a speed of 3000 rpm for 12 min.
2) After removing the supernatant, 20 mL of cementation solution (containing equimolar of $CaCl_2$ and urea) of various concentrations (1.0 M, 1.3 M, 1.6 M, 1.8 M and 2.0 M) were added to the centrifuge tubes.
3) The centrifuge tubes were then shaken continuously at a speed of 200 rpm and the calcium concentration of the cementation solution was measured after 24 h, 48 h and 72 h according to the standard method 2340C, which involves titrating the samples with ethylene diamine tetraacetate dehydrate (V. Stabnikov, et al, *Cem. Concr. Res.*, 2011, 41, 1143-1149). All tests were conducted in duplicate.

Figure 3:
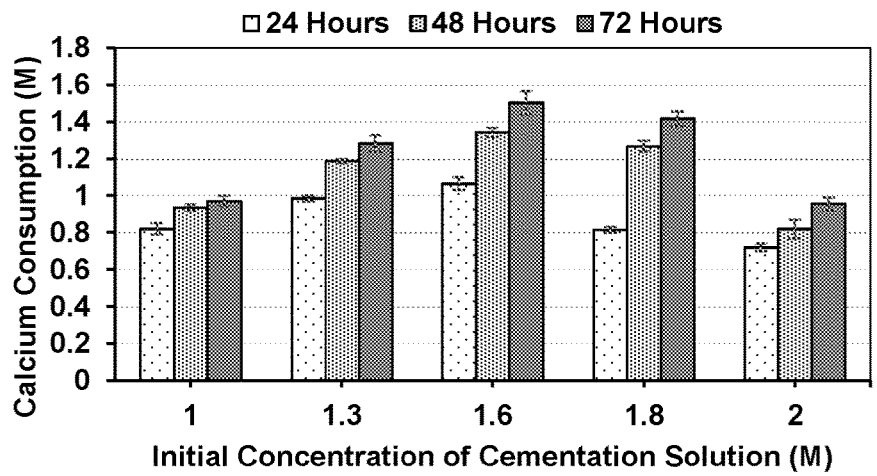
FIG. 3 Depicts the effect of different concentrations of cementation solution (1.0 M, 1.3 M, 1.6 M, 1.8 M and 2.0 M) on the calcium consumption of the urease-active bioslurry at 24 h, 48 h and 72 h respectively.

In this study, the effect of the concentrations of cementation solution on the chemical conversion efficiency of the bioslurry was tested. As shown in FIG. 3, the calcium consumption of the bioslurry increased with an increase in the calcium concentration up to 1.6 M, and was followed by a gradual decrease with subsequent increase in the calcium concentration. This was probably due to the toxic effect of the high concentration of calcium ions on the urease-producing bacteria (S. C. Brooks, et al., *Environ. Sci. Technol.*, 2003, 37, 1850-1858). The maximum calcium consumption was determined to be about 1.44 M in 72 h for an initial concentration of calcium of 1.6 M with the maximum precipitation rate of 1.03 mole/L/day. Therefore, 1.6 M was chosen as the optimal concentration for $CaCO_3$ production in the subsequent examples.

Example 3. Effect of Different Concentrations of the Cementation Solution ($Ca^{2+}$ and Urea) in Reducing the Permeability of the Bioslurry-Induced Water Barriers Method The urease-active bio-slurry was prepared according to Example 1, using 0.4 M of urea and $CaCl_2$). The solid content of the residual mixture was determined to be 25±3 wt. %.

Twelve transparent acrylic columns (50 mm inner diameter and 100 mm in length) were placed vertically with the bottom of the columns covered by a plastic cap with an open outlet so that the columns were kept under free draining conditions.

To evaluate the effect of the concentration of the cementation solution ($Ca^{2+}$ and urea) on the permeability reduction, a series of urea and $CaCl_2$) with various concentrations ranging from 1.0 to 1.8 M (containing equimolar of $CaCl_2$) and urea) were prepared. The preparation of each sand column comprised the following three sequential steps:
1) packing and compacting 150 g of Ottawa sand in the transparent acrylic column;
2) placing 15 mL of the produced urease-active bio-slurry (25 wt. % solid content, 60 U/g) on the surface of the Ottawa sand.
   The liquid solution contained in the bio-slurry penetrated into the Ottawa sand, leaving a dry bio-slurry on the sand surface forming a slurry layer of 2-3 mm thick; and
3) gently placing an additional 100 g of Ottawa sand on the top of the bio-slurry layer. The top sand layer had a void ratio of 0.7 or a void volume of 20 $cm^3$.

The sand columns were treated using four different concentrations of cementation solution of 1.0 M, 1.3 M, 1.6 M and 1.8 M respectively. For each concentration of solution, a permeability test was conducted after the first, second and third treatment. In total, twelve tests were carried out.

For the first treatment, the cementation solution (mixture of urea and $CaCl_2$) solution, 40 mL) was percolated through the top of the column. Excess solution was drained from the outlet at the bottom. Then the sand columns were kept at room temperature (25±1° C.) for 24 h, followed by the second supply of the urea and $CaCl_2$) solution of the same volume and concentration. The third supply was carried out after 48 h. Both the second and third supplies of the urea and $CaCl_2$) solution were 20 mL in volume.

Results and Discussions

Figure 4:
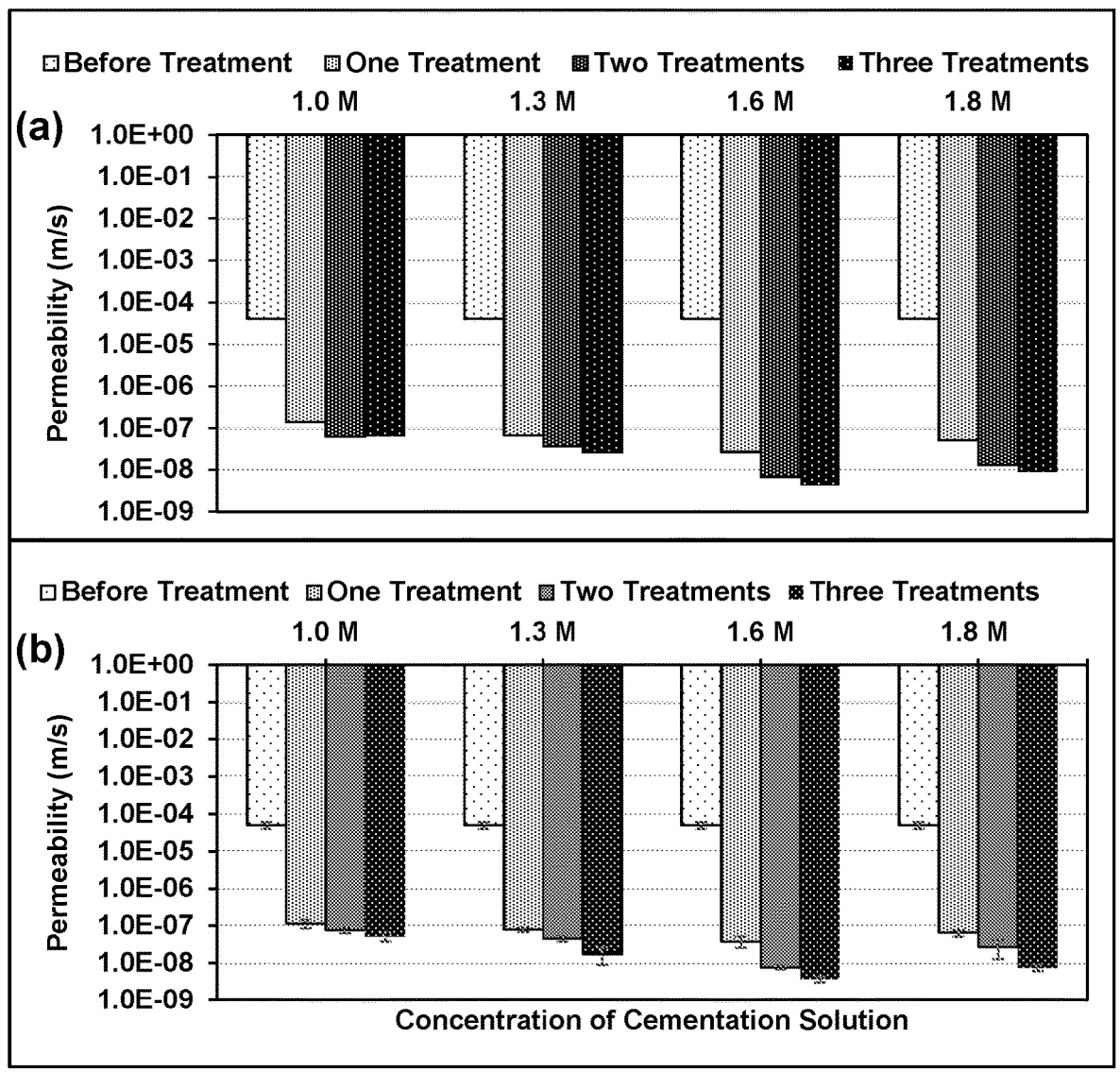
FIG. 4 Depicts the effect of different concentrations of cementation solution (1.0 M, 1.3 M, 1.6 M and 1.8 M) in reducing the permeability of the bioslurry-induced water barrier after one to three treatments, with (a) and (b) representing the initial and optimised results respectively.

In the initial studies, the permeability of the water barrier formed from the urease-active bio-slurry decreased dramatically. It was also observed that a concentration of 1.6 M for each of urea and $CaCl_2$ solution was the optimal concentration, as it reduced the permeability of the sand from the original value of $4.1 \times 10^{-4}$ m/s for untreated sand to $2.7 \times 10^{-8}$ m/s after the first treatment (FIG. 4a). The permeability of sand can be further decreased by increasing the number of treatments. For example, after three treatments, the permeability of the bio-treated soil was reduced to $4.3 \times 10^{-9}$ m/s, which is as low as that for clay.

Similarly, in subsequent optimised studies, the results obtained for the permeability of the treated columns is as shown in FIG. 4b. The reduction in permeability was dependent on the concentration of cementation solution as well as the number of treatments applied. As shown in FIG. 4b, the reduction in permeability was significant even with one treatment. The second and third treatment would lead to further reduction in permeability. It was also observed that the lowest permeability of $3.6 \times 10^{-9}$ m/s was obtained for samples treated three times using the concentration at 1.6 M. Thus, the optimum concentration was 1.6 M as it resulted in lowest permeability, which was consistent with the results shown in Example 2 and FIG. 3.

Example 4. Effect of Having a Top Sand Layer and Varying the Thickness of the Layer on the Permeability of the Bioslurry-Induced Water Barrier To evaluate the effect of the top sand in reducing the permeability of the bioslurry-induced water barrier, studies were carried out using the column set up as described in Example 3. The urease-active bio-slurry was prepared following the instruction indicated in the above Example 1.

Initial Studies

In the initial studies, sand columns with and without a top overlaid sand were used. The sand columns were each treated with 40 mL of the mixture of urea and $CaCl_2$) solution (1 M) and were kept at room temperature for 24 h. This is then followed by the second supply of urea and $CaCl_2$) solution of the same volume and concentration. The third supply was carried out after 48 h. After the treatments were completed, the permeability of the bioslurry-induced water barrier were evaluated. As shown in FIG. 5a, the reduction in the permeability of the bioslurry-induced water barrier without the overlaid porous materials was about three magnitudes less as compared to that having the overlaid porous materials. This suggests that having the overlaid porous materials on top of the bioslurry layer can significantly enhance the efficiency of the treatment, and hence reduce the permeability of the bioslurry-induced water barrier drastically.

Subsequent Optimised Studies (Including Investigating the Effects of Various Thickness of Top Sand Layer)

In further optimised studies, additional tests without the top sand layer were carried out using cementation solution of 1.6 M by following the same procedure as described in Example 3. Additionally, the effect of varying the thickness of the top sand layer was also evaluated. Three columns with different thickness of top sand layer of 1.5 cm (50 g sand with void volume of 10 $cm^3$), 3 cm (100 g sand with void volume of 20 $cm^3$) and 6 cm (200 g sand with void volume of 40 $cm^3$) were treated three times using the cementation solution of 1.6 M. The permeability of each column was measured after each treatment.

Figure 5:
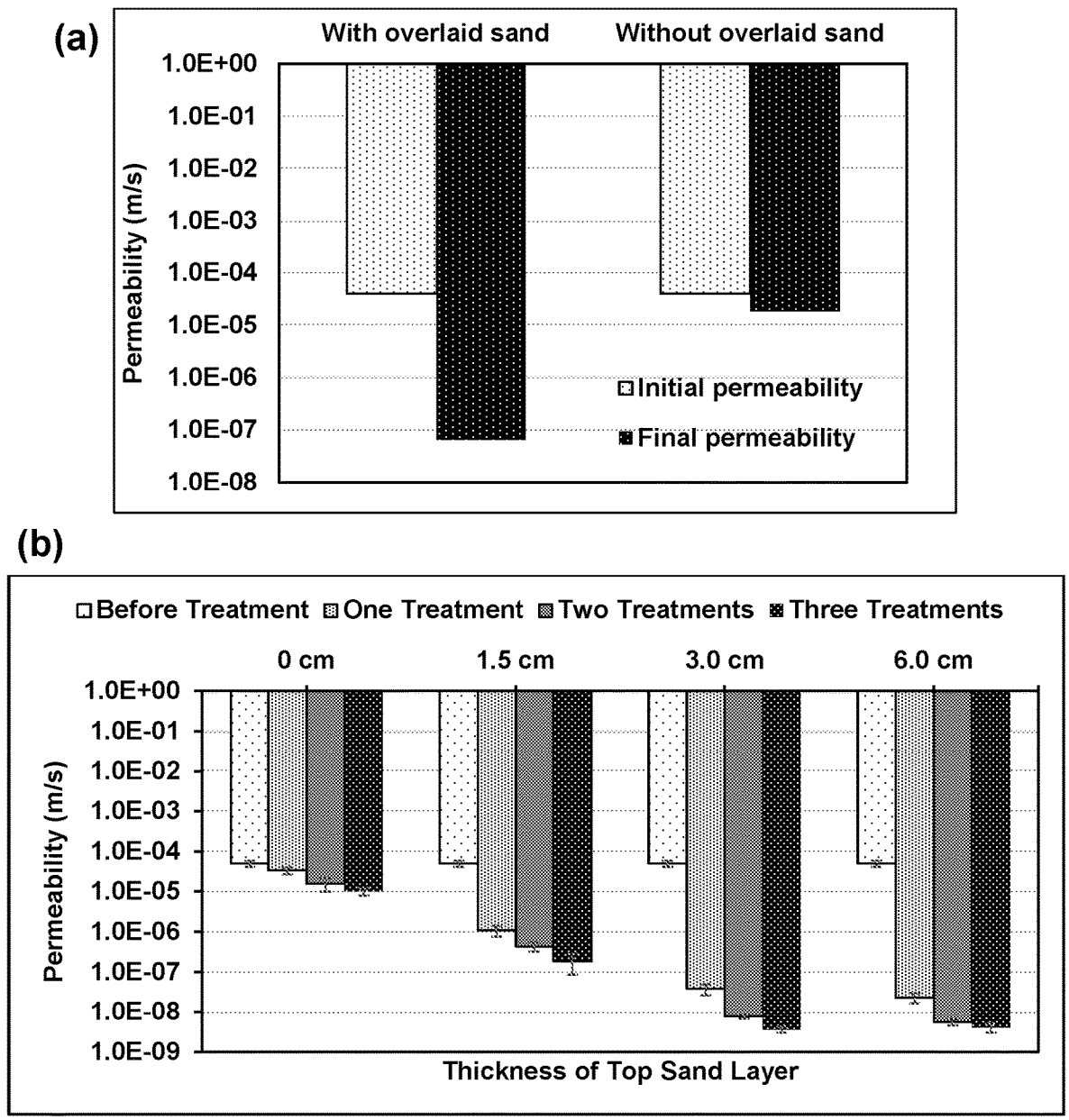
FIG. 5 Depicts: (a) the initial results of having an overlaid porous material on top of the bioslurry layer in reducing the permeability of the bioslurry-induced water barrier; and (b) the subsequent optimised results of varying the thickness of the top sand layer in reducing the permeability of the water barrier.

The effect of the thickness of the top sand layer on permeability reduction are shown in FIG. 5. It was observed that in the absence of the top sand layer, the reduction of the permeability was significantly less effective as compared to those columns with the top sand layer. This was probably due to the top sand layer prolonging the time for cementation solution to diffuse through the top sand to reach the bioslurry layer. Therefore, this resulted in a sustained continuous biocementation, rather than an instantaneous supply of the cementation solution in the case without the top sand layer.

For the sand column without the top sand layer, the cementation solution flowed through the bioslurry layer rapidly, which was too fast to allow sufficient calcium carbonate precipitation. The sand layer can prolong the time for biocementation in the bioslurry layer to precipitate more $CaCO_3$ crystals through diffusion. Therefore, the urease-active bioslurry layer can receive a continuous supply of urea and calcium ions through the chemical diffusion, resulting in a sustained MICP process.

The effect of various thickness of the sand layer on permeability of the bioslurry-induced water barrier layer was also studied by comparing the permeability of the water barrier layer formed using 1.5 cm, 3 cm and 6 cm of the top sand layers respectively, under the same conditions. It can be seen from FIG. 5 that the effect in the reduction of permeability varied with the thickness of the sand layer. The permeability of the water barrier with 1.5 cm of top sand layer was reduced to approximately $10^{-7}$ m/s after three treatments. However, with a thicker top sand layer of 3 cm and 6 cm, the permeability of the water barrier were reduced to $10^{-9}$ m/s. The difference in the permeability was probably due to the thinner 1.5 cm top sand layer that can only retain 10 mL of the cementation solution, which was insufficient to precipitate enough $CaCO_3$ crystals to reduce the permeability further. Although both the 3 cm and 6 cm top sand layer provided sufficient cementation solution and a more sustained MICP, the maximum precipitation rate of the bioslurry was probably reached using this thickness of top sand layer (3 to 6 cm). This suggests that having a top sand layer thicker than 6 cm is probably unnecessary as this will result in higher material costs.

Example 5. Effects of Desiccation on the Permeability and Durability of the Bioslurry-Induced Water Barrier Method To evaluate the effect of desiccation on the permeability of the bioslurry-induced water barrier, studies were carried out using the column set up as described in Example 3. A sand column was treated three times following the steps in Example 3, using the optimised concentration of the cementation solution (1.6 M). The urease-active bio-slurry was prepared following the instruction indicated in the above Example 1.

After treatments were completed, the permeability of the bioslurry-induced water barrier was measured and recorded. The column was then dried in the oven at 70° C. for 7 days and the permeability was re-determined. It was also observed that drying at 70° C. for 1 day gave the same result. This process was repeated four times to assess the durability of bioslurry-induced water barrier and any possibility of shrinkage that may be caused by desiccation.

In contrast, additional two sand columns overlaid with 3 cm and 6 cm of compacted clay liner (with 40% moisture content) respectively were prepared separately. These two thicknesses were chosen because a thin clay liner can be easily damaged even at low water head during permeability test. The initial permeability of both columns with clay liner were determined to be close to $10^{-9}$ m/s. This was then followed by the desiccation cycles with permeability measurements as described above.

Results and Discussions

The durability of the bioslurry-induced water barrier was evaluated after several desiccation cycles and was also compared with that of a clay liner. Typically, it is common for the permeability of compacted clay liner to achieve $10^{-9}$ m/s, or even lower at a certain range of water content. However, clay liner can undergo irreversible shrinkage upon desiccation at relatively arid sites, and result in cracking and increase in permeability (D. E. Daniel and Y.-K. Wu, *J. Geotech. Eng.*, 1993, 119, 223-237). As the permeability of the clay linear can only be maintained for several days during the wet-dry period, this poses stability and durability concern when clay is used in field application (D. E. Daniel, *J. Geotech. Eng.*, 1984, 110, 285-300).

Figure 6:
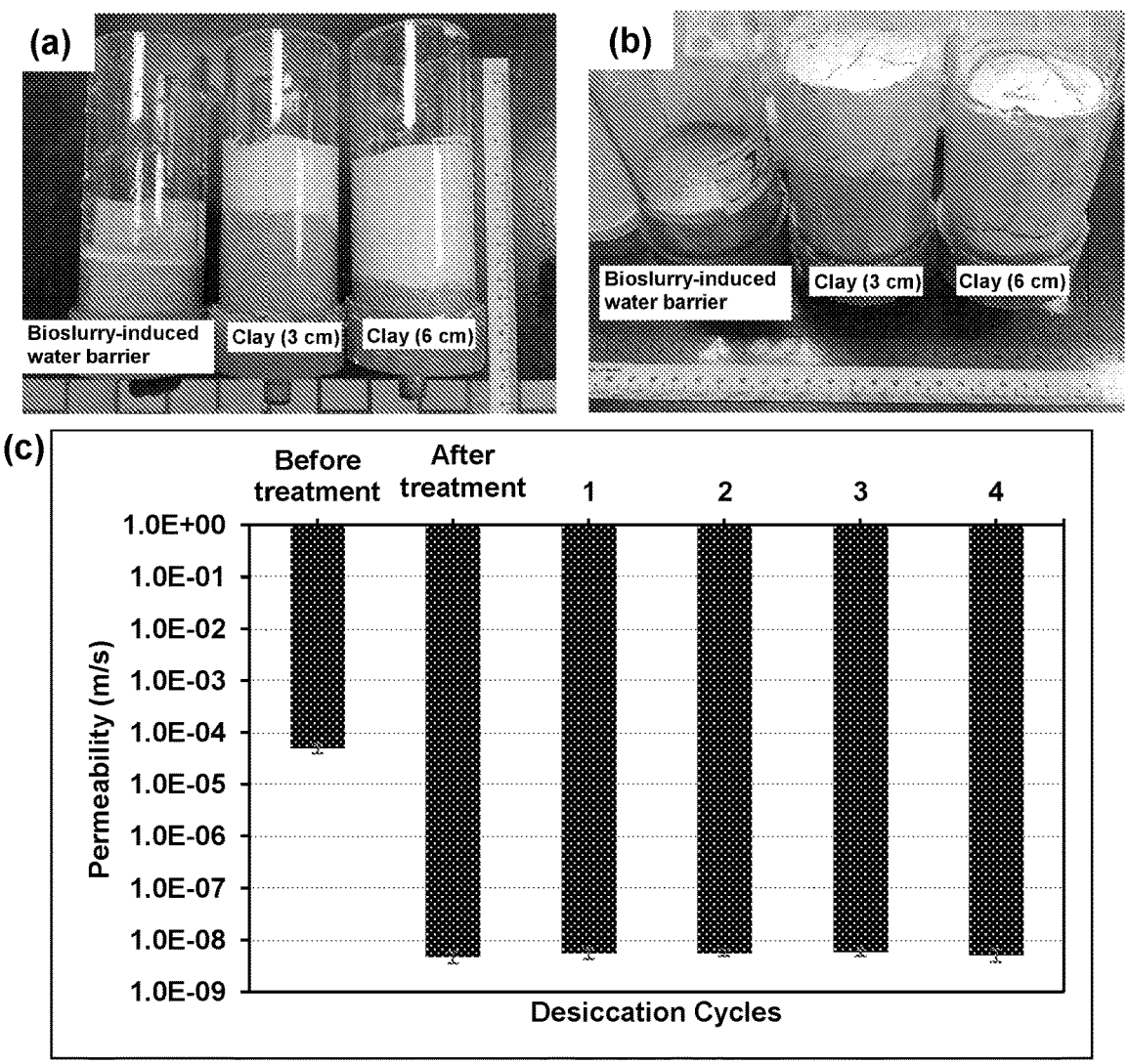
FIG. 6 Depicts: (a and b) photographs comparing a bioslurry liner with a clay liner of 3 cm and 6 cm thick, respectively, that had undergone desiccation; and (c) the permeability of the sand columns after three treatments with the cementation solution (1.6 M), and subsequently one to four desiccation cycles.

FIGS. 6a and b show the photographs of the sand columns with a thin bioslurry-induced water barrier (with top sand removed), clay liners of 3 cm and 6 cm thick, respectively, which had been subjected to four cycles of the desiccation process. As shown in FIG. 6b, many cracks were formed on the clay liners.

The permeability of the 3 cm thick clay liner (after compacted) was determined to be $1.1 \times 10^{-8}$ m/s. It was also observed that the clay liner cracked after desiccation, and the cracks led to an increase in infiltration of water, therefore resulting in an increase in the permeability up to $1.6 \times 10^{-5}$ m/s. Similarly, the permeability of the 6 cm thick clay liner increased from the initial $5.7 \times 10^{-9}$ m/s to $4.7 \times 10^{-6}$ m/s after desiccation, due to shrinkage of the clay which resulted in cracks. This was because that surface tension effects at the air-water-solid contacts inside the clay generated negative pore water pressure (positive suctions), which resulted in clay contraction, and ultimately caused clay shrinkage with cracking after desiccation (C. J. Miller, H. Mi, and N. Yesiller, *J. Am. Water Resour. Assoc.*, 1988, 34, 677-686). The desiccation process resulted in large cracks and these significantly increased the permeability of the clay layer.

In contrast, the bioslurry-induced water barrier formed an extremely dense and thin $CaCO_3$ liner, which reduced the permeability significantly. The $CaCO_3$ liner also exhibited better stability and durability than clay liner under cycled desiccated process. This is because MICP not only contributed to the bonding strength in bioslurry-induced water barrier, but also produced pore filling effect which resulted in lower permeability. The $CaCO_3$ crystals precipitated throughout the sand matrix, therefore bridging adjacent particles and providing sufficient bonding strength. Although the bioslurry was made up of free calcium carbonate particles with entrapped urease-active bacteria, the water barrier was predominately formed due to the precipitated crystals at the gaps between the $CaCO_3$ grains. It was observed that further treatments by cementation solution filled up most gaps between $CaCO_3$ grains which lowered the permeability. This resulted in a water barrier which has better hydraulic properties than clay.

As shown in FIG. 6c, the permeability of sand was dramatically reduced from an initial value of $4.04 \times 10^4$ to $4.3 \times 10^{-9}$ m/s after treatments to form the bioslurry-induced water barrier. It can be seen from FIG. 6c that the low permeability of the barrier was not damaged by the drying process, as shown by the relatively constant permeability of $4.6 \times 10^{-9}$ m/s throughout the repeated drying cycles.

Example 6. Healing of Cracks on the Bioslurry-Induced Water Barrier

Method

In order to devise a way to repair damaged bioslurry liner, healing tests were carried out using additional four columns, following the column set up and treatments (using 1.6 M of the cementation solution) as described in Example 3. The urease-active bio-slurry was prepared following the instruction indicated in the above Example 1.

A dry sand column was treated once using 40 mL of cementation solution (1.6 M). When the first treatment was completed, the topping sand was removed and cracks were then created by dropping free falling body onto the bioslurry-induced water barrier. The permeability before and after crack initiation were both measured. Thereafter, 100 g of clean and dry Ottawa sand was added on top of cracked bioslurry liner, followed by repeated treatments (three times) of 20 mL of cementation solution (1.6 M), with the permeability of the sand column measured after each treatment.

After each treatment, the sand columns were kept at room temperature ($25 \pm 1°$ C.) for 48 h to allow sufficient reaction prior to permeability test.

Results and Discussions

It is possible to damage the bioslurry-induced water barrier during the construction process. For example, pre-hardened bioslurry-induced water barrier may be accidently hit by a free falling body, or damaged by people who unintentionally stepped on the overlaid porous material before the bioslurry-induced water barrier was hardened. Both sceneries may result in cracks and can lead to failure of the water barrier.

Figure 7:
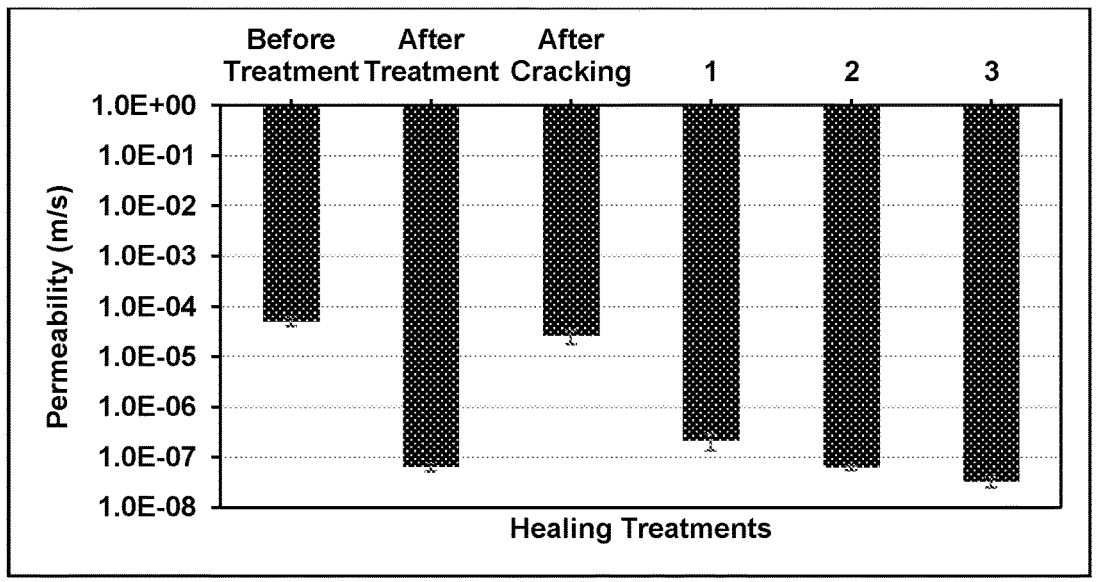
FIG. 7 Depicts the permeability of bioslurry-induced water barrier after cracks were induced on the water barrier, and after one to three healing treatments of the cracked barrier using the cementation solution (1.6 M).

Therefore, it is essential to devise ways to repair the damaged bioslurry-induced water barrier to improve the lifespan of the barrier and to determine the recoverability of such water barriers. It was found that cracked bioslurry-induced water barrier with high permeability could be healed with further treatments with cementation solution which restored the low permeability of the barrier, indicating good recoverability. FIG. 7 shows the permeability of bioslurry-induced water barrier before and after cracking, as well as the decrease in permeability with the increasing number of treatments during the healing process.

The permeability of the treated sand column increased from $7.6 \times 10^{-8}$ m/s to $1.8 \times 10^{-5}$ m/s after the cracks were formed. A significant reduction in the permeability was observed after each treatment as shown in FIG. 7. Subsequently, the permeability of bioslurry-induced water barrier was recovered to the level of $10^{-8}$ m/s after three treatments. This was due to the cracks of the bioslurry layer gradually filled up with the newly induced calcite crystals which sealed the cracks and restored the low permeability. Therefore, the undesirable effects of the cracks on the permeability can be mitigated through repair by continuously supplying cementation solution when bacteria cells are still active. Furthermore, when the bacteria are inactive after a long term of operation, the crack can also be healed through MICP process by adding new bacteria together with the cementation solution.

Example 7. Characterisation of the Bioslurry and Bioslurry-Induced $CaCO_3$ by Scanning Electron Microscopy (SEM)

As different concentrations of cementation solution can result in different extents of permeability reduction of the bioslurry-induced water barrier, it is therefore of interest to understand the morphology of the $CaCO_3$ crystals of the bioslurry and the density of the crystals induced in the grain matrix of the precipitated $CaCO_3$ water barrier by SEM analysis.

Method

The representative samples of the bioslurry (of Example 1, not treated with cementation solution) and the bioslurry-induced water barrier (of Example 3) were rinsed with tap water and oven dried at 105° C. for 24 h prior to characterisation by SEM. The $CaCO_3$ crystals from the bioslurry-induced precipitation were observed using a scanning electron microscope (Zeiss EV050, UK).

Results and Discussions

Figure 8:
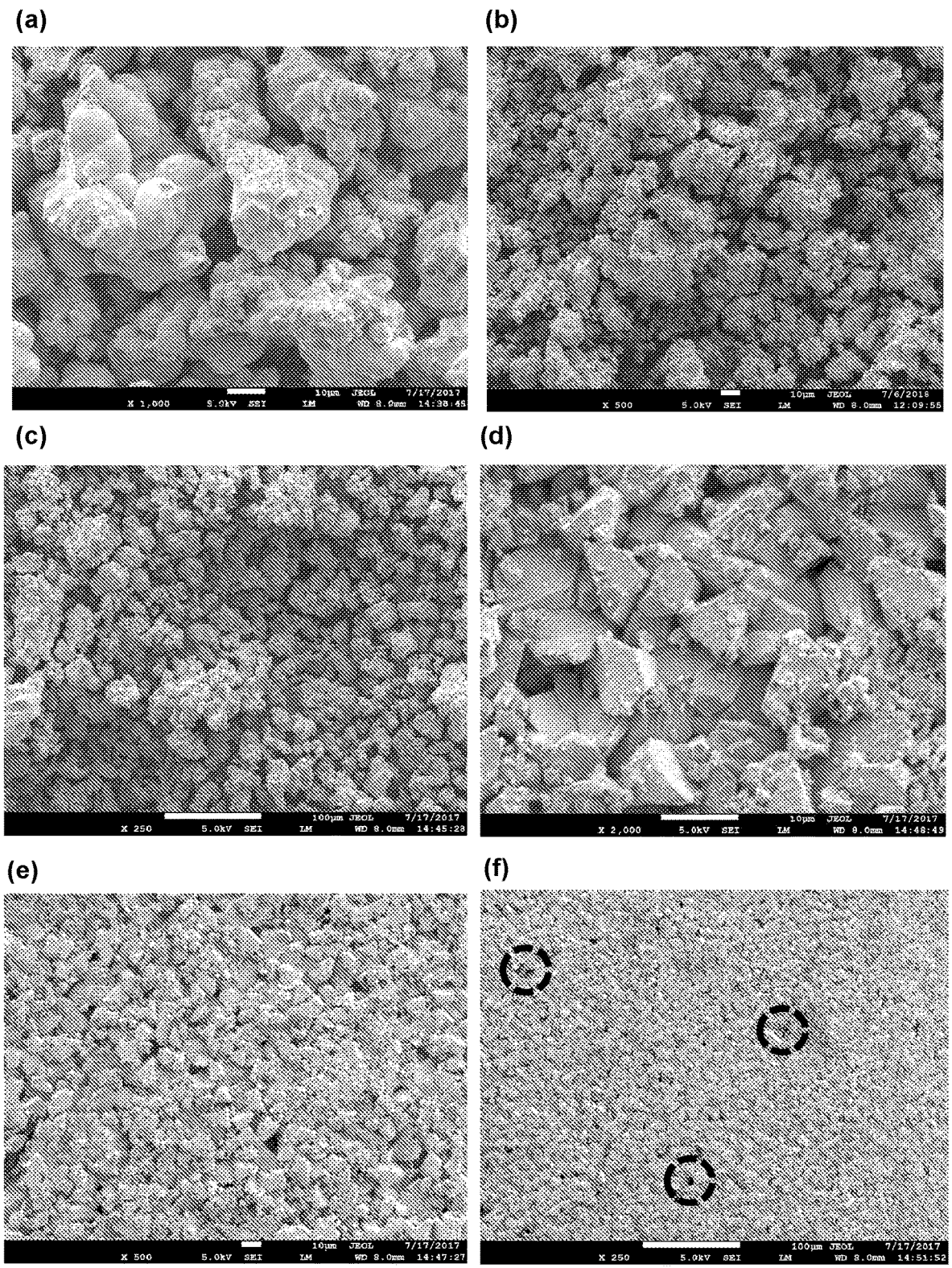
FIG. 8 Depicts: (a-c) the SEM images of the bioslurry at 1000×, 500× and 250× magnification respectively; and (d-f) the SEM images of the bioslurry-induced water barrier at 2000×, 500× and 250× magnification respectively. The dashed circles in (f) indicate the pores on the surface of the water barrier.

The SEM images of the bioslurry sample examined at three different magnifications (250×, 500× and 1000×) are shown in FIG. 8a-c. It was observed that the crystals were mainly spherical in shape with particle size of around 0.2 to 5 μm (FIG. 8c). Small clusters of crystals of approximately 10 to 20 μm were observed and the clusters appear to be loosely packed with little or only weak bonding among them, which probably resulted in the high permeability of the bioslurry layer (in the order of $10^{-5}$ m/s).

The SEM images of the bioslurry-induced water barrier layer, (i.e. the bioslurry layer with more $CaCO_3$ crystals precipitated due to the MICP process) are as shown in FIG. 8d-f, in three different magnifications. The crystals generally have rhombohedral shape which are similar to the shape of the crystals precipitated by ureolytic bacteria (J. J. De Yoreo, P. M. Dove, *Science*, 2004, 306, 1301-1302; S. Al-Thawadi, R. Cord-Ruwisch, *J. Adv. Sci. Eng. Res.*, 2012, 2, 12-26; L. Cheng, M. A. Shahin, *Can. Geotech. J.*, 2016, 53, 1376-1385). The rhombohedral shaped crystals with various sizes from 5 to 15 μm have filled in the pores of the spherical-shaped $CaCO_3$ particles of the bioslurry and appears to be bonded together between the two types of crystals to form a densely packed matrix as shown in FIG. 8d.

Comparing FIGS. 8b and c with FIGS. 8e and f, it appears that the number of pores among the calcium carbonate crystals of the bioslurry-induced water barrier was significantly less than that of the bioslurry. For example, the SEM image of FIG. 8f shows the presence of only a few tiny gaps (circles) in the $CaCO_3$ layer which probably accounts for the low permeability of the bioslurry-induced water barrier. Given this, this suggests that the cementation solution plays an important role in lowering the permeability of the bio-cemented bioslurry layer (in the order of $10^{-8}$ m/s), as compared to the untreated bioslurry.

Example 8. Model Test of the Bioslurry-Induced Water Barrier in a Glass Tank

To understand the effectiveness of the bioslurry-induced water barrier in a more practical setting, the experiment was conducted at a larger scale (i.e. in a larger glass tank) to investigate the effect of bioslurry-induced $CaCO_3$ precipitation on the seepage rate. This example represents a prospective application of the invention for use in aquacultural ponds that require low water permeability, which can be achieved by the bioslurry-induced water barrier. In addition, the bioslurry-induced water barrier requires less material, such as fewer treatments by ureolytic bacteria and cementation solution, as compared to conventional biocemented crust or liner (V. Stabnikov, et al., *Cem. Concr. Res.*, 2011, 41, 1143-1149).

Method

A glass tank with dimension of 39×24×27 cm was used for the model test. The tank was divided into two separate compartments by a plastic plate and a filter was glued to the bottom glass below the plastic plate, which retained the sand but allowed water to seep through. Before filling one of the compartments with sand, the side gap between glass and plate was also thoroughly glued to prevent leaking from the sides. The biocementation of model test was then carried out following the steps below, which are similar to the column test in Example 3, but different in the amount of materials used.

1) 8 kg of Ottawa sand was packed into one of the compartments of the tank to form a 10 cm thick groundwork, with the surface leveled.
2) 260 mL of bioslurry (of Example 1, 25% solid content, (60 U/g)) was uniformly pipetted onto the surface of sand, which built up a 3-4 mm thin bioslurry layer.
3) Additional 2 kg Ottawa sand was placed onto the surface of the bioslurry layer, and the sand was saturated with 400 mL of 1.6 M cementation solution as 1.0 void volume of topping sand.
4) An additional 400 mL of cementation solution (1.6 M) was supplied to allow for percolation by gravity and capillary force right after the first supply of cementation solution. Excess solution could be drained out from the bottom filter.
5) Repeated treatments of cementation solution were conducted to achieve an effective water barrier at 24 h, 48 h and 72 h.
6) After the fourth treatments was completed, topping sand was removed prior to the determination of the seepage rate.

The seepage rate is defined as the daily loss rate (cm/day) of water permeate the bioslurry layer. It was determined by the change in water level per day in the water tank. The initial water level was at 22 cm and the residual water depth was recorded regularly for a period of 30 days. This provides a useful indication of the reduction of permeability in a large scale model test using the bioslurry-induced water barrier.

Results and Discussions

Figure 9:
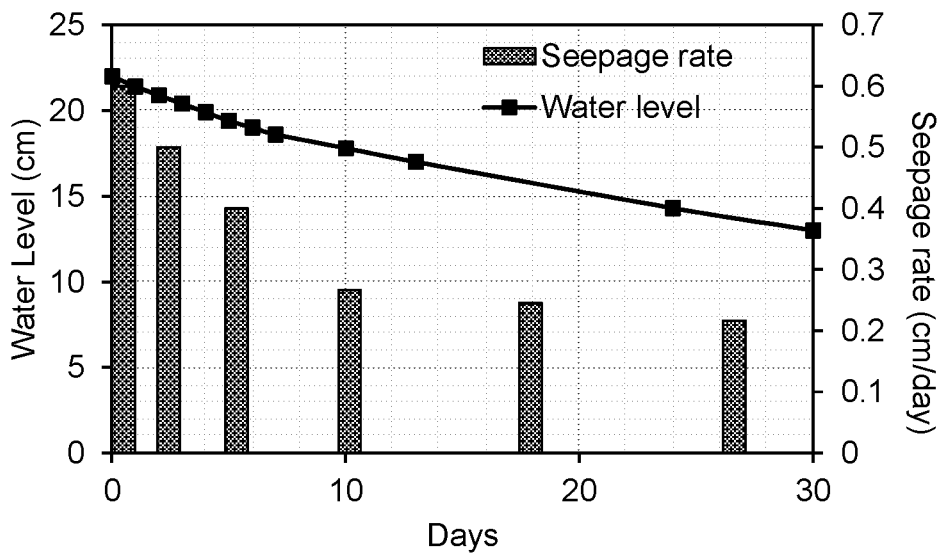
FIG. 9 Depicts the decrease in water level and the seepage rate of the model test of the bioslurry-induced water barrier in a glass tank for a period of one month.

As shown in FIG. 9, it was found that the daily seepage rate decreased gradually over a period of one month. The seepage rate decreased with a decrease in water level, from about 0.6 cm/day at the start of the test to about 0.21 cm/day near the end of the test period. Indeed, the sealing effect was promising and the average daily seepage rate was about 3 mm/day. It was also noted that the seepage rate included the evaporation of water from the tank as the measurement was conducted at room temperature. Therefore, the actual seepage rate could potentially be lower, if the loss of water due evaporation was not considered. Advantageously, it is noted that the current seepage rate is generally lower than the mean seepage rate of water pond, which ranges from 19 to 58 mm/day for the tropical fish ponds, and 136 to 182 mm/day for the shrimp mariculture ponds (V. Stabnikov, et al., *Cem. Concr. Res.*, 2011, 41, 1143-1149; D. Teichert-Coddington, et al, *Aquacultural Engineering*, 1988, 7, 309-320; R. S. Weisburd and E. A. Laws, *Aquacultural Engineering*, 1990, 9, 377-403).

Example 9. Determining the Flexural Strength of the Bioslurry-Induced Water Barrier In addition to having a reduced permeability of the soil, the high mechanical strength of the bioslurry-induced water barrier is also a highly desired property to support high hydrostatic pressure and to prevent bending of the liner (V. Stabnikov, et al., *Cem. Concr. Res.*, 2011, 41, 1143-1149). Flexural strength, also known as modulus of rupture, measures the structural stability of hard-setting surface soils and the susceptibility of a soil to crusting, which is strongly correlated to soil permeability and workability (N. McKenzie, K. Coughlan, and H. Cresswell, *Soil physical measurement and interpretation for land evaluation* vol. 5: Csiro Publishing, 2002).

Method

To assess the feasibility of this construction material, the flexural strength of the bioslurry-induced water barrier of Example 8 was tested via a three-point loading test. After demolishing the model test, the bioslurry liner was trimmed into nine specimens with a length of 6 to 10 cm, width of 3 to 5 cm and a thickness of 0.1 cm. The modulus of rupture was calculated using the following equation (N. McKenzie, K. Coughlan, and H. Cresswell, *Soil physical measurement and interpretation for land evaluation* vol. 5: Csiro Publishing, 2002):

$$R = \frac{3PL}{2bd^2} \quad (1)$$

where P is the load (force) at the fracture point; L is the length of the support span; b is the width; and d is thickness of the specimen.

The results were plotted via Matlab and presented in agreement with the position.

Results and Discussions

Figure 10:
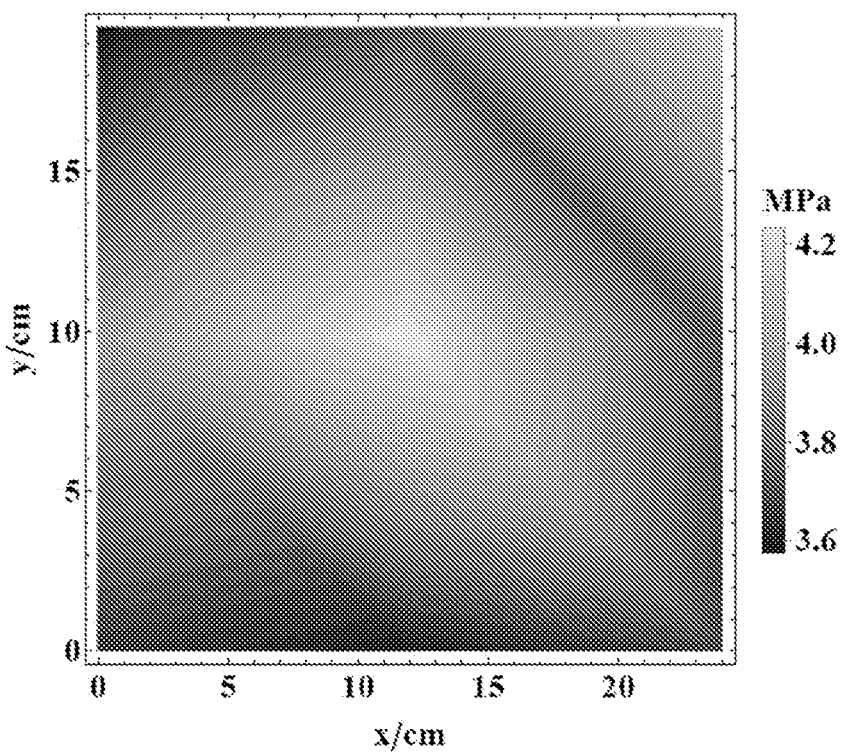
FIG. 10 Depicts the distribution of the modulus of rupture on a sample of the water barrier, obtained from the model test, in a three-point flexural test.

The average modulus of rupture for the bioslurry liner was determined to be 4 MPa, as obtained from the nine different specimens trimmed from the bioslurry liner at various locations after the model test. As shown in FIG. 10, it was observed that the strength distribution of the as-formed bioslurry liner is homogenous and that the modulus of rupture is sufficient to support high hydrostatic pressure of up to hundred meters. This suggests that the bioslurry liner is strong enough to withstand the hydrostatic pressure for ponds or reservoirs. It was also noted that the modulus of rupture of the bioslurry liner is significantly higher than that for other liner construction materials, which suggests the superior flexural strength of the bioslurry liner to withstand high pressure. For example, the hydrostatic resistance for PVC plastic liners used for pond sealing is typically from 0.4 to 1.0 MPa (V. Stabnikov, et al., *Cem. Concr. Res.*, 2011, 41, 1143-1149), and 0.03 MPa for an 8 cm thick consolidated clay (N. Thusyanthan, et al., Geotechnique, 2007, 57, 581-594).

The invention claimed is:

1. A process of forming an inorganic water barrier layer on top of a porous substrate in need thereof, the process comprising the steps of:
   (a) providing a porous substrate having a top surface;
   (b) depositing a urease-active slurry onto the top surface of the porous substrate to form a bioslurry layer, the urease-active slurry comprising an aqueous suspension of particles of a water-insoluble inorganic material that is impregnated with urease-active bacteria, where the formed bioslurry layer includes the particles of the water-insoluble inorganic material; and
   (c) subjecting the bioslurry layer to one or more treatments with an aqueous solution comprising urea and a water barrier source material to convert the bioslurry layer into an inorganic water barrier layer;
   wherein the resulting inorganic water barrier layer has a water permeability in the order of from $10^{-10}$ to $10^{-5}$ m/s.

2. The process according to claim 1, wherein the process further comprises a step of covering the bioslurry layer of step (b) with a layer of a porous material that has a surface, where the one or more treatments of step (c) are initially applied to the surface of the porous material.

3. The process according to claim 2, wherein the porous material is selected from one or more of the group consisting of sand, soil and rocks.

4. The process according to claim 2, wherein the resulting inorganic water barrier layer has a water permeability in the order of from $10^{-10}$ to $10^{-6}$ m/s.

5. The process according to claim 2, wherein the porous material layer has a thickness of greater than 1.5 cm.

6. The process according to claim 2, wherein when there are two or more treatments with an aqueous solution comprising urea and a water barrier source material in step (c) of claim 1, each treatment is separated by a period of time of from 1 hour to 72 hours.

7. The process according to claim 1, wherein the urease-active slurry has a solid content of from 5 to 80% w/w.

8. The process according to claim 1, wherein the porous substrate is selected from one or more of the group consisting of a cracked inorganic water barrier layer, sand, soil, and rocks.

9. The process according to claim 1, wherein the water-insoluble inorganic material is a metal carbonate.

10. The process according to claim 9, wherein the metal of the metal carbonate is selected from one or more of the group consisting of Ca, Mg, and Al.

11. The process according to claim 9, wherein the metal carbonate is $CaCO_3$.

12. The process according to claim 1, wherein the water barrier source material is selected from one or more of the group consisting of a metal chloride, a metal acetate, a metal lactate, and a metal nitrate.

13. The process according to claim 12, wherein the metal in the water barrier source material is selected from one or more of the group consisting of Ca, Mg, and Al.

14. The process according to claim 13, wherein the metal is calcium.

15. The process according to claim 1, wherein the aqueous solution comprises a molar ratio of urea:water barrier source material of from 1:20 to 20:1.

16. The process according to claim 1, wherein each of the urea and the water barrier source material independently have a concentration of from 0.1 to 2 mol/L.

17. The process according to claim 16, wherein there is an equimolar concentration of urea and water barrier source material in the aqueous solution.

18. The process according to claim 1, wherein the bioslurry layer and the inorganic water barrier layer independently have a thickness of from 0.5 to 25 mm.

19. The process according to claim 1, wherein the urease activity of the urease-active slurry is from 10 to 1500 U/g.

20. The process according to claim 1, wherein the bioslurry layer formed in step (b) has a water permeability in the order of $10^{-5}$ m/s.

21. The process according to claim 1, wherein the modulus of rupture of the inorganic water barrier layer is 2 to 10 MPa when measured using a sample of the layer that is 0.1 mm thick and has a length of from 6 to 10 cm and a width of from 3 to 5 cm.

* * * * *